United States Patent
Farmer et al.

(10) Patent No.: US 9,861,775 B1
(45) Date of Patent: Jan. 9, 2018

(54) EMERGENCY RESUSCITATION APPARATUS WITH EXTERNAL VOLUME CONTROL

(71) Applicants: Charles A. Farmer, Tulsa, OK (US); Tammy L. Maras, Tulsa, OK (US)

(72) Inventors: Charles A. Farmer, Tulsa, OK (US); Tammy L. Maras, Tulsa, OK (US)

( * ) Notice: Subject to any disclaimer, the term of this patent is extended or adjusted under 35 U.S.C. 154(b) by 0 days.

(21) Appl. No.: 15/411,697

(22) Filed: Jan. 20, 2017

(51) Int. Cl.
*A61M 16/00* (2006.01)
*A61M 16/06* (2006.01)

(52) U.S. Cl.
CPC .... *A61M 16/0075* (2013.01); *A61M 16/0084* (2014.02); *A61M 16/06* (2013.01); *A61M 2205/3379* (2013.01); *A61M 2205/583* (2013.01); *A61M 2205/586* (2013.01)

(58) Field of Classification Search
CPC .................................................. A61M 16/0084
See application file for complete search history.

(56) References Cited

U.S. PATENT DOCUMENTS

| | | | |
|---|---|---|---|
| 3,890,967 A * | 6/1975 | Elam .................. | A61M 16/00 128/205.17 |
| 4,176,663 A * | 12/1979 | Hewlett ............... | A61M 16/00 128/204.26 |
| 4,898,166 A | 2/1990 | Rose et al. | |
| 5,345,929 A * | 9/1994 | Jansson ............ | A61M 16/0084 128/205.13 |
| 5,711,295 A | 1/1998 | Harris, II | |
| 6,155,257 A | 12/2000 | Lurie et al. | |
| 7,121,279 B2 * | 10/2006 | Dennis ................. | A61M 16/06 128/203.29 |
| 7,658,188 B2 | 2/2010 | Halpern et al. | |
| 8,235,043 B2 | 8/2012 | Halpern | |
| 8,443,804 B2 | 5/2013 | Lee et al. | |
| 8,936,024 B2 | 1/2015 | Pearce | |
| 2014/0318544 A1 | 10/2014 | Murphy et al. | |

* cited by examiner

*Primary Examiner* — Rachel Young
(74) *Attorney, Agent, or Firm* — Dale J. Ream

(57) ABSTRACT

An emergency resuscitation apparatus with external air volume control includes a housing having top and bottom plates pivotally coupled so as to siphon air into an internal reservoir via an inflow port and propel air out through an outlet port to a patient. A volume control plate is coupled to the bottom plate externally adjacent a second end wall, the volume control plate having a plurality of volume selectors. An air volume limit arm is operatively coupled to the volume control plate and selectively movable between and coupled to a selected volume selector. A volume limiting flange associated with the volume limit arm are positioned in a common vertical plane with top plate such that the volume limit flange prevents upward movement of the top plate beyond the setting of the volume limit arm so as to regulate a quantity of air being expelled.

20 Claims, 15 Drawing Sheets

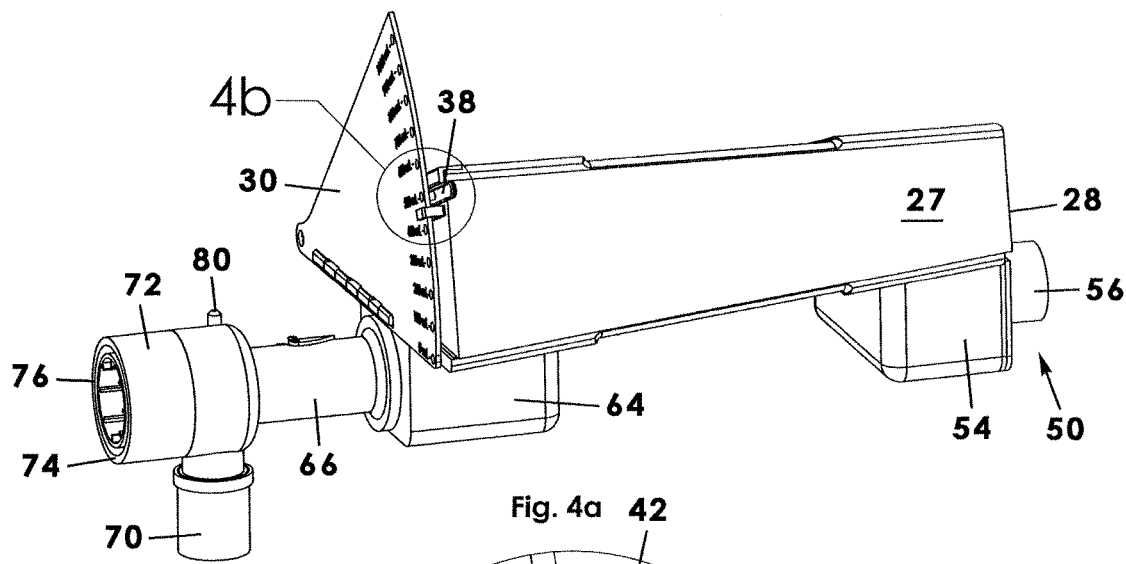
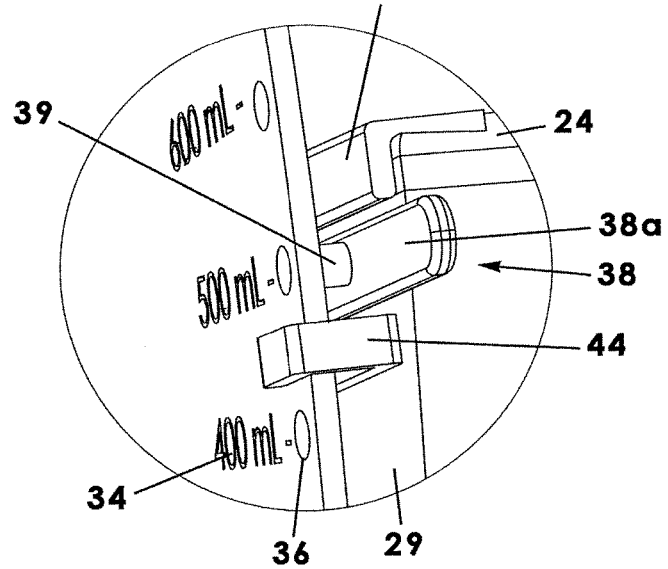
Fig. 4a
Fig. 4b

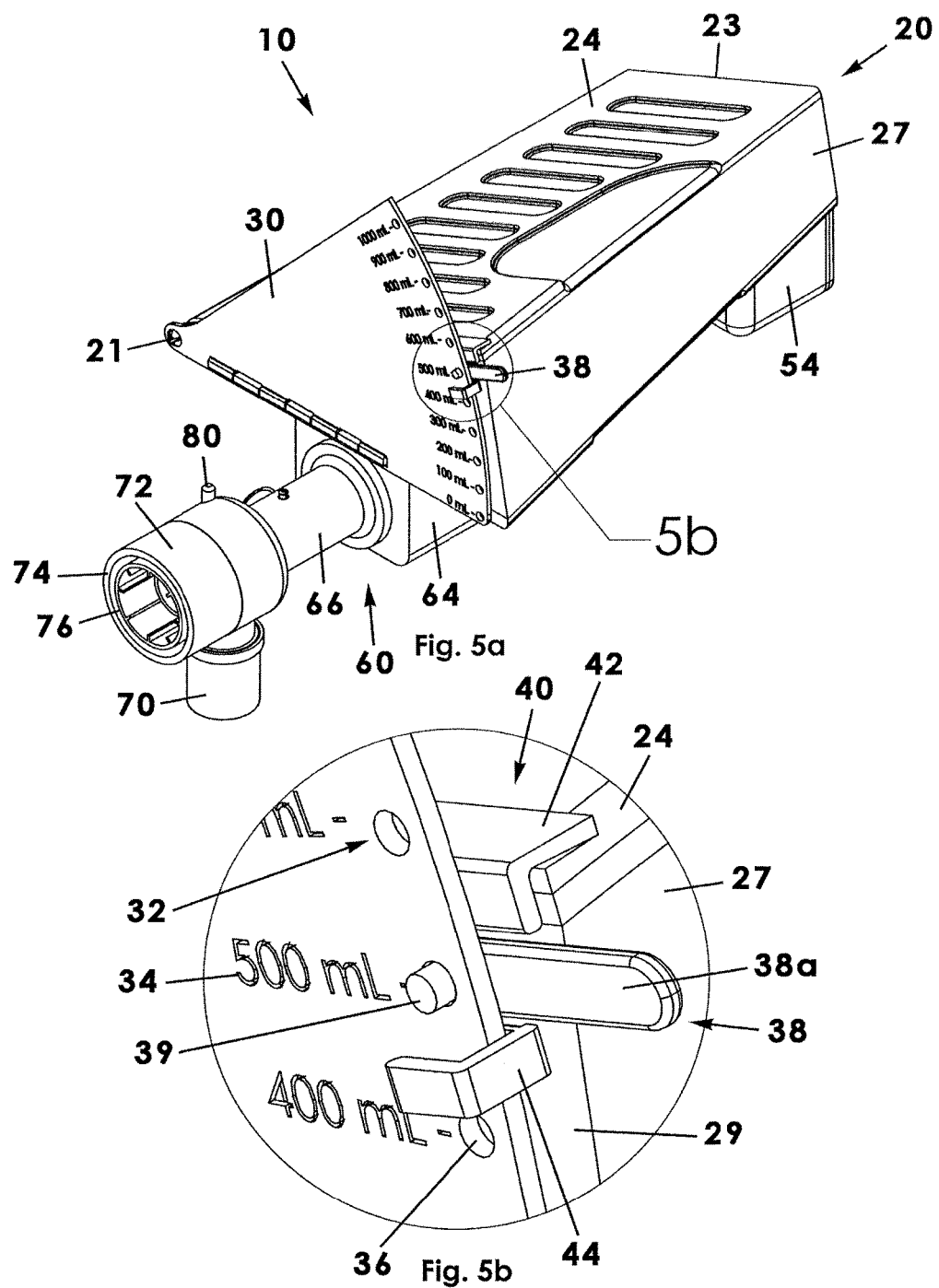

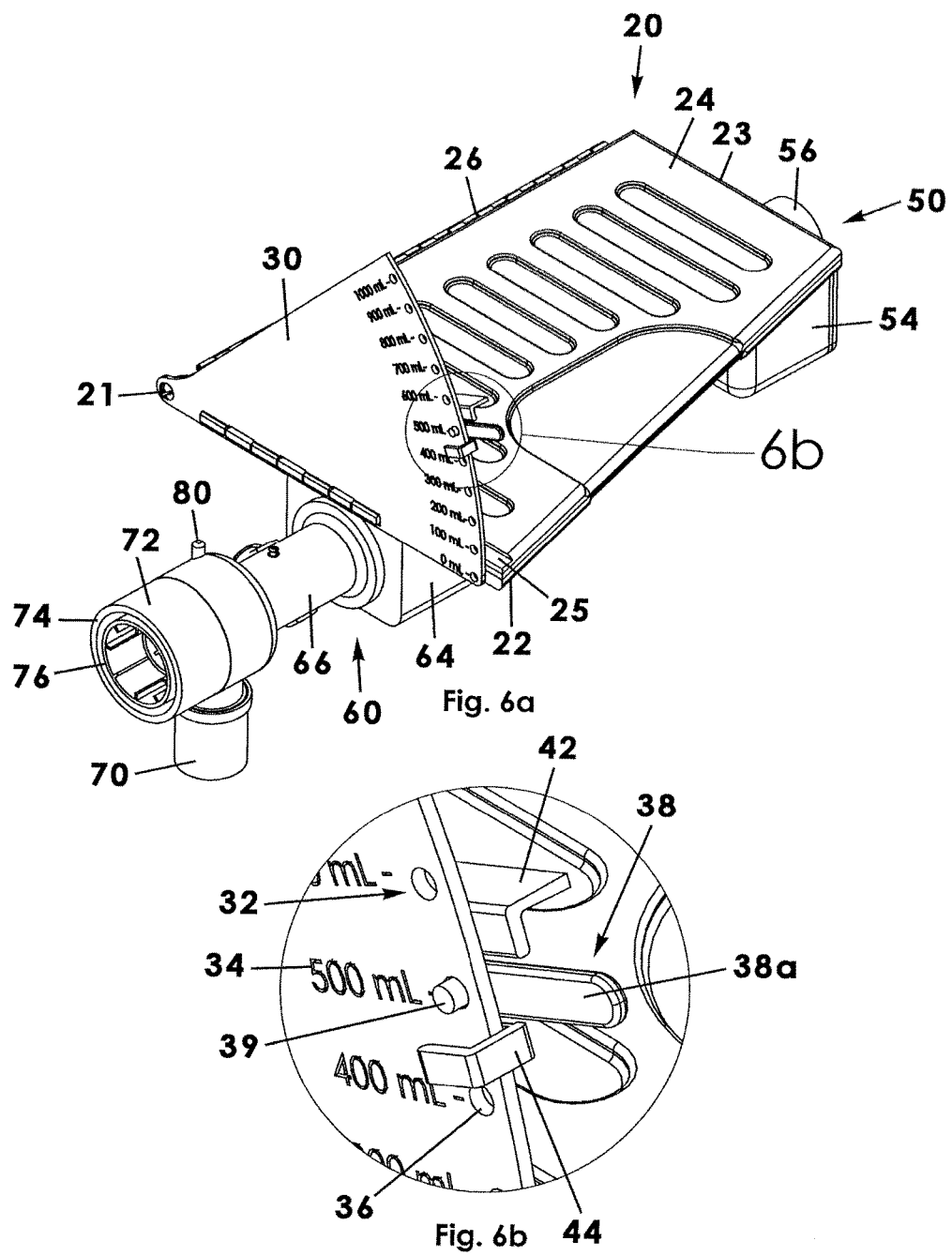

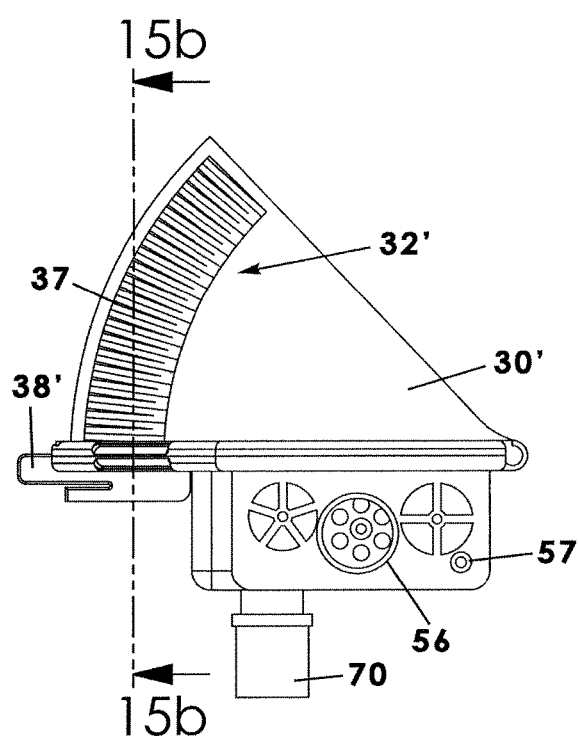
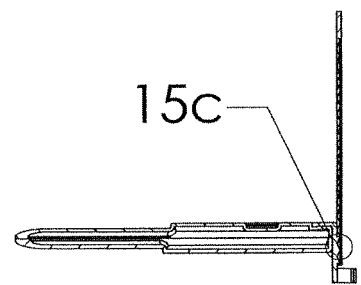
Fig. 15b
Fig. 15a

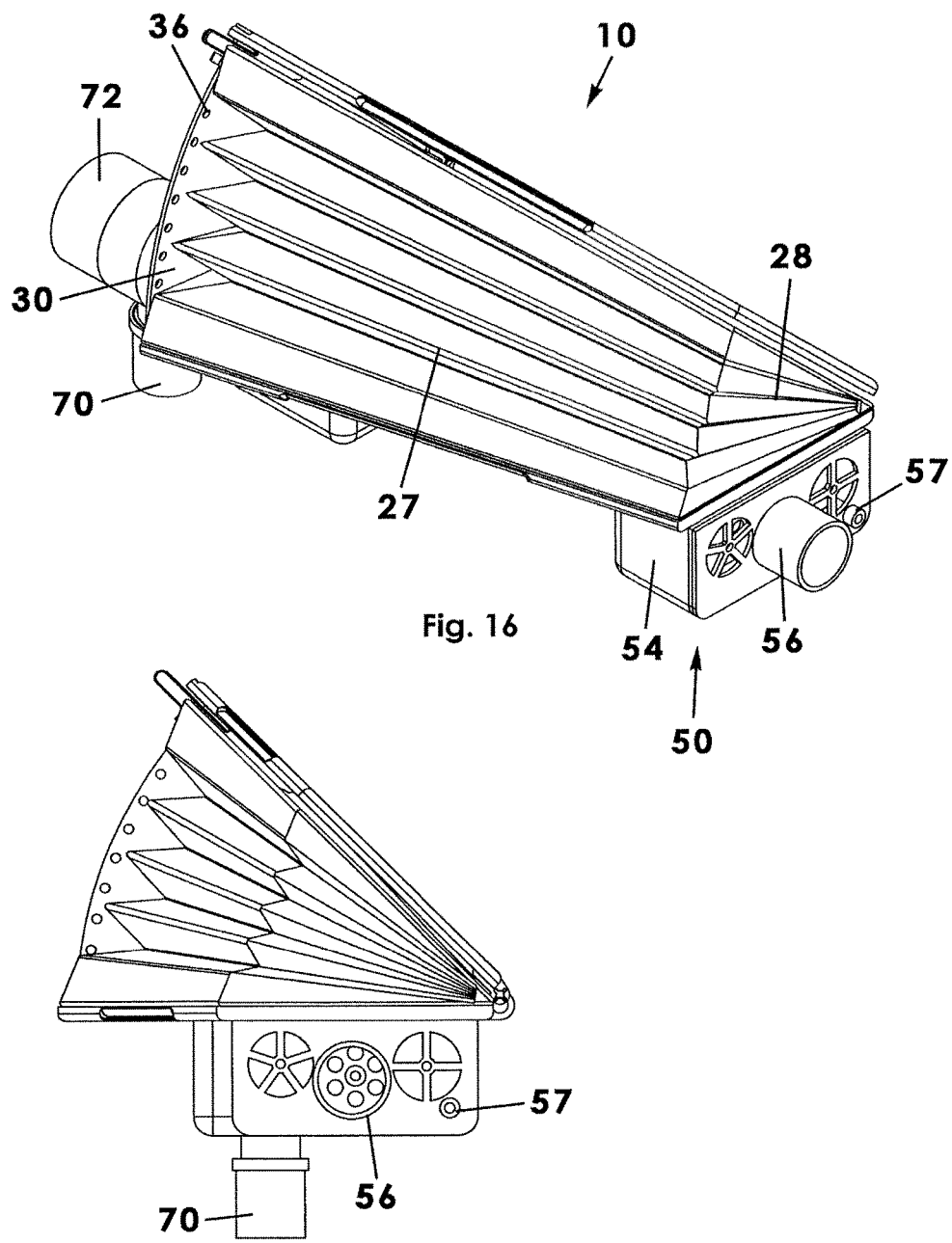

EMERGENCY RESUSCITATION APPARATUS WITH EXTERNAL VOLUME CONTROL

BACKGROUND OF THE INVENTION

This invention relates generally to resuscitation devices and, more particularly, to an emergency resuscitation apparatus having an external assembly for setting a volume of air expelled from an outflow port as may be appropriate based on the size or age of a patient.

An emergency resuscitator is a portable device, commonly referred to as a bag-valve-mask, that may be manually operated to repeatedly inflate the lungs of a patient who is in pulmonary arrest, i.e. is not breathing on his own or in patients in respiratory distress secondary to inadequate ventilation and are in need of ventilator assistance. The use of a portable resuscitator, whether in a hospital setting or at the scene of a medical emergency, can be the difference between life or death.

The current resuscitator as it is currently designed was invented in 1953 and was first marketed in 1956. Therefore, there has been no significant design or functional advancement in this device in 60 years.

One problem with current bag-valve-mask resuscitator devices is that they can potentially expel volumes of air significantly larger than that appropriate for the patient. For instance, the lung capacity of a full-grown man is much larger than the capacity of an infant or a child. It is common, with the current technology, for a manufacturer to produce three different sizes of resuscitators: adult, child and infant. To prevent causing injury while using a resuscitator, this requires medical personnel to either choose one of these portable resuscitators specifically designed and adapted for the approximate size of the patient, or simply "estimate" how much to squeeze the resuscitator bag. The potential for causing injury to a patient due to lung over expansion, therefore, is obvious.

The design of the current resuscitator is extremely inefficient. As an example, current resuscitator devices designed for use in the adult patient have air reservoirs containing volumes of approximately 1600-1800 ml depending on the manufacturer. However, they are designed to deliver only 500-700 ml with each squeeze or activation of the device. This allows for a residual amount of air retained in the bag of approximately 1000 ml and therefore, if used improperly, can result in significant over inflation of the patient's lungs and potentially causing alveolar damage. Similar reservoir volume vs volume delivered discrepancies exist with the child and infant versions of the device.

Another deficiency associated with the current manual resuscitator design concept is inconsistency/reproducibility of the volume of air delivered with each activation. The design (football shaped, which is ergonomically extremely poor) and the reservoir volume versus volume delivered discrepancy create an environment where it is extremely difficult, and almost impossible, for the current devices to perform up to published specifications regarding delivered volumes in a consistent and reproducible way in multiple scenarios. Several examples can be cited. First would be differences found when the same device is activated by two different operators who have different size hands and different grip strengths. A second would be seen when the same operator repeatedly activates the same device over time wherein a degree of grip fatigue and strength would have a definite impact. A third would be the fact that during a resuscitation procedure, the operator does not consciously concentrate on the activation function of the device because his/her attention is directed elsewhere. Still another fact is that volume delivered specifications vary as much as 100 to 150 ml per activation of the adult version from manufacturer to manufacturer, therefore, producing a volume delivered discrepancy from device to device.

One portable resuscitator that is the subject of U.S. Pat. No. 8,936,024 recognized a need to selectively limit a volume of air expelled from an outlet. Although presumably effective for its intended use, the '024 patent utilizes a complicated assembly that includes a myriad of index pins positioned in a void and multiple cords and cord anchors which must be set to infant, child, or adult settings. The setting of the volume controls of the '024 design are limited to these three approximate volume settings and do not provide for more incremental volume selections for appropriate use. Another significant disadvantage of the '024 design is that in the event of a malfunction of the internal structure of the volume control mechanism it would not be visible to and may not be detected by the operator, because there would be no external indication of the malfunction, making it possible to deliver an inappropriate volume of air to the patient (either too low or too high).

Therefore, it would be desirable to have an emergency resuscitator apparatus having an external control mechanism for limiting a maximum volume of air to be expelled each time a bellows is operated and that delivered volume be more accurate and reproducible than the current technology allows. Further, it would be desirable to have an emergency resuscitator apparatus that may be set to a specific volumetric level (measured in milliliters) to be expelled by the apparatus. Also, it would be desirable to have an emergency resuscitator apparatus that may be set to a multitude of volume settings as compared to only three settings available in the '024 design in order to accommodate the desirable expelled volumes of air calculated for various sizes of individuals that lie between and over those settings provided for by the '024 design. In addition, it would be desirable to have an emergency resuscitator apparatus having a volume limiting flange that prevents the opening of a top plate of a bellows beyond an amount corresponding to a selected volume of air to be expelled by the resuscitator thereby providing a safety mechanism preventing over inflation of the lungs.

SUMMARY OF THE INVENTION

An emergency resuscitation apparatus with external air volume control according to the present invention includes a housing that includes a bottom plate having opposed side edges and that includes a top plate having opposed side edges, wherein a respective side edge of the bottom plate is pivotally coupled to a respective side edge of the top plate so that the bottom and top plates are selectively movable in an accordion fashion between open and closed positions. The housing includes opposed first and second end walls coupled to corresponding front and rear edges of the bottom and top plates, respectively, so that the housing defines an interior area. It is understood that the housing operates as a bellows and may be in the form of a pleated bag as shown in the accompanying drawings.

An inflow port is operatively coupled to the housing proximate the first end wall and in fluid communication with the interior area and with air outside the interior area and configured so that ambient air is siphoned into the interior area upon actuation of the top plate away from the bottom plate. An outflow port is operatively coupled to the housing proximate the second end wall and in fluid communication with the interior area and configured so that air in the interior area is expelled from the interior area upon actuation of the top plate toward the bottom plate.

A volume control plate is coupled to the bottom plate and extending upwardly and positioned externally adjacent the second end wall, the volume control plate having a plurality of volume selectors. A volume limit arm is operatively coupled to the volume control plate and selectively movable between and selectively coupled to a selected volume selector. A volume limiting flange is proximate to the front edge of the top plate, the volume limiting flange and the volume limit arm being positioned in a common vertical plane such that the volume limit arm prevents upward movement of the top plate beyond the setting of volume limit arm.

Therefore, a general object of this invention is to provide a resuscitation apparatus having a bellows configuration with an external mechanism providing for the setting of a maximum volume of air expelled from a patient port upon each actuation of the bellows.

Another object of this invention is to provide a resuscitation apparatus, as aforesaid, in which the housing of the bellows may include a pleated bag arrangement.

Another object of this invention is to provide a resuscitation apparatus, as aforesaid, in which the housing of the bellows is operated from a side angle.

Still another object of this invention is to provide a resuscitation apparatus, as aforesaid, having an external volume limit arm that enables a user to select a volume of air to be expelled upon each subsequent operation of the bellows.

Yet another object of this invention is to provide a resuscitation apparatus, as aforesaid, having a volume limiting flange that prevents the top plate of the bellows from opening to receive ambient air beyond the setting of the volume limit arm.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2b is an isolated view on an enlarged scale taken from FIG. 2a;

FIG. 3b is an isolated view on an enlarged scale taken from FIG. 3a;

FIG. 4a is another perspective view of the resuscitation apparatus as in FIG. 2a, illustrated with a volume limit arm in a disengaged configuration and with the limit arm adjacent another selector of the volume plate;

FIG. 4b is an isolated view on an enlarged scale taken from FIG. 4a;

FIG. 5a is a perspective view of the resuscitation apparatus as in FIG. 4a, illustrated with the volume limit arm in a fully engaged configuration;

FIG. 5b is an isolated view on an enlarged scale taken from FIG. 5a;

FIG. 6a is another perspective view of the resuscitation apparatus as in FIG. 5a, illustrated with a volume limit arm in an engaged configuration and with the housing in a fully closed (compressed) configuration;

FIG. 6b is an isolated view on an enlarged scale taken from FIG. 6a;

FIG. 7b is a sectional view taken along line 7b-7b of FIG. 7a;

FIG. 8b is a sectional view taken along line 8b-8b of FIG. 8a;

FIG. 15a is an inflow end view of the resuscitation apparatus of FIG. 14;

FIG. 15b is a sectional view taken along line 15b-15b of FIG. 15a;

FIG. 16 is a perspective view of the resuscitation apparatus as in FIG. 3a, illustrated with the housing in the form of a pleated bellows; and FIG. 17 is an inflow end view of the resuscitation apparatus as in FIG. 16.

DESCRIPTION OF THE PREFERRED EMBODIMENT

Figure 1:
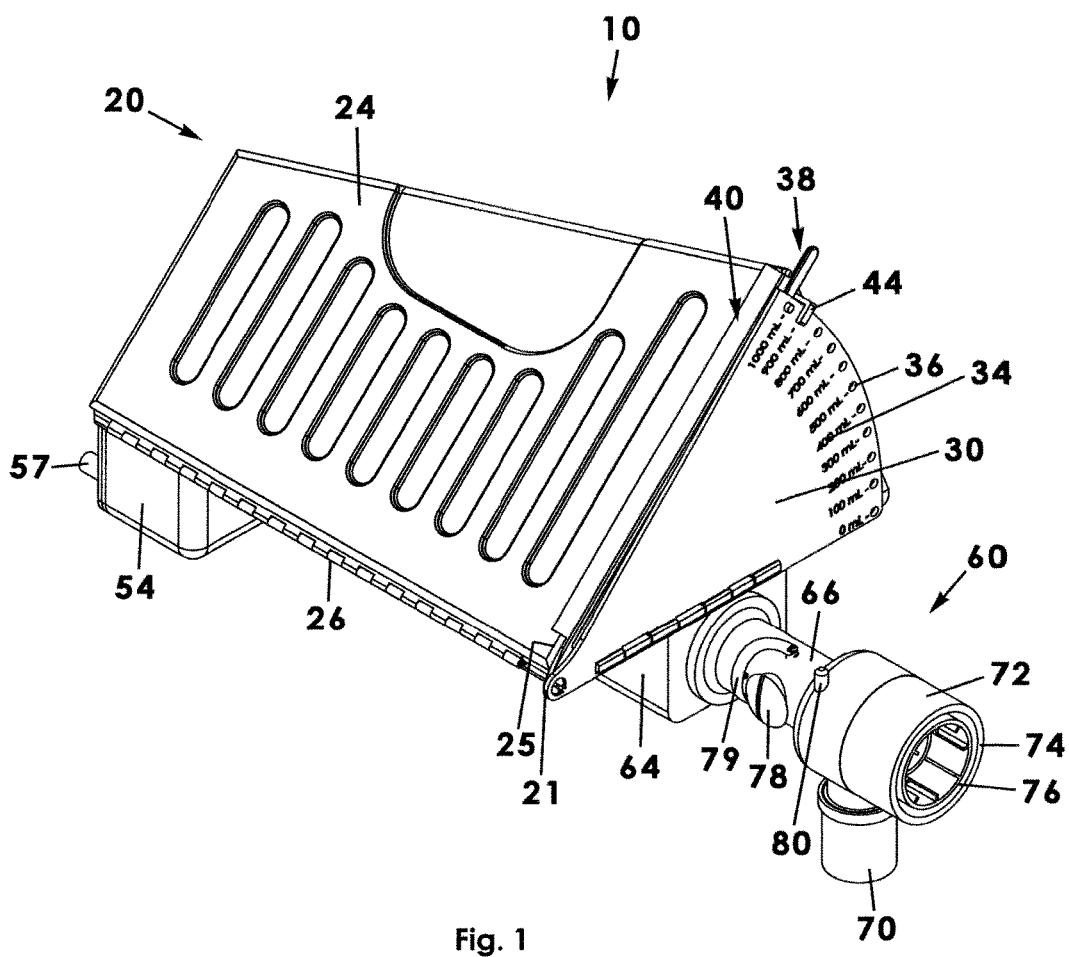
FIG. 1 is a perspective view of an emergency resuscitation apparatus according to a preferred embodiment of the present invention.

An emergency resuscitation apparatus with external air volume control according to a preferred embodiment of the present invention will now be described in detail with reference to FIGS. 1 to 17 of the accompanying drawings. The resuscitation apparatus 10 includes a housing 20 having top and bottom plates pivotally coupled together in the manner of bellows, an inflow port 50 and an outflow port 60 in fluid communication with an interior of the housing 20, a volume control plate 30, a volume limit arm 38, and a volume limiting flange 40 such that a quantity of air driven out through the outflow port 60 may be controlled via an external setting.

By way of defining terms used in this application, it is understood that what is referred to as the "bottom plate" is a firm bottom surface and what is referred to as the "top plate" is a firm top surface. In other words, the firm surfaces have the characteristic of firmness based on the mold and material with which they are fabricated in manufacturing.

The housing 20 may also be referred to as a bellows as it is configured to siphon or suck ambient air into an interior area via an inflow port 50 and to force air out of the interior area through an outflow port 60 upon operation of pivotally coupled top and bottom plates. Further, the bellows or housing may include a pleated bag configuration (FIG. 16). More particularly, the housing 20 may include a bottom plate 22 having a generally planar configuration and a top plate 24 also having a generally planar configuration. Each plate includes a pair of elongate opposed side edges. Corresponding proximal side edges of the bottom plate 22 and top plate 24 are pivotally coupled together. Preferably, the pivotal connection may be a molded or fused spine 26, although a living hinge, traditional hinge, or other pivotal coupling techniques may also work.

Figure 2A:
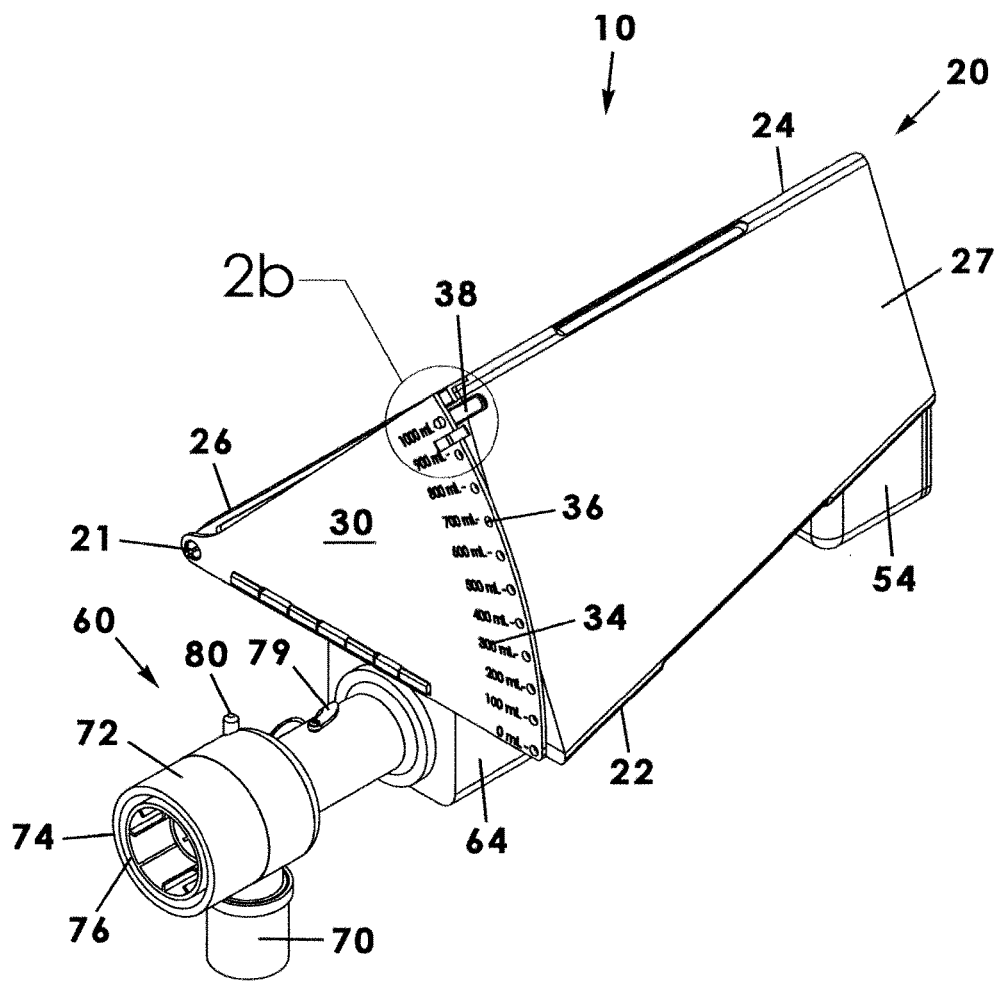
FIG. 2a is a perspective view from another angle of the resuscitation apparatus as in FIG. 1, illustrated with a volume limit arm in a fully engaged configuration relative to a volume control plate.

A flexible and selectively compressible bellows wall 27 is coupled to respective distal side edges of the bottom plate 22 and top plate 24 and extends therebetween (FIG. 2a). Similarly, a first end wall 28 and a second end wall 29 having a flexible construction extend between rear 23 and front 25 edges of bottom plate 22 and top plate 24, respectively (reference numeral 23 being used to designate rear edges of both the bottom plate 22 and top plate 24; reference numeral 25 being used to designate front edges of both the bottom plate 22 and top plate 24. The collapsible structures may be in the form of folding in an accordion manner or in the nature of a pleated bag. In combination, the bottom plate 22, top plate 24, bellows wall 27, first end wall 28, and second end wall 29 define an interior area of the housing 20 capable of receiving selectable quantities of ambient air as will be described in more detail below.

The pivotal coupling, such as the molded spine 26, between proximal side edges of the bottom plate 22 and top plate 24 defines an imaginary horizontal axis about which the top plate 24 is pivotally movable between open and closed configurations relative to the bottom plate 22. Subject to the limitations of the volume limit arm 38 and volume limiting flange 40 described later, the top plate 24 may be moved between a fully open configuration (FIG. 1) and a fully closed configuration (FIG. 6a). It is understood that the degree to which the top plate 24 is allowed to move toward the fully open configuration is dependent upon a selected position of the volume limit arm 38, as will be described below.

Figure 14:
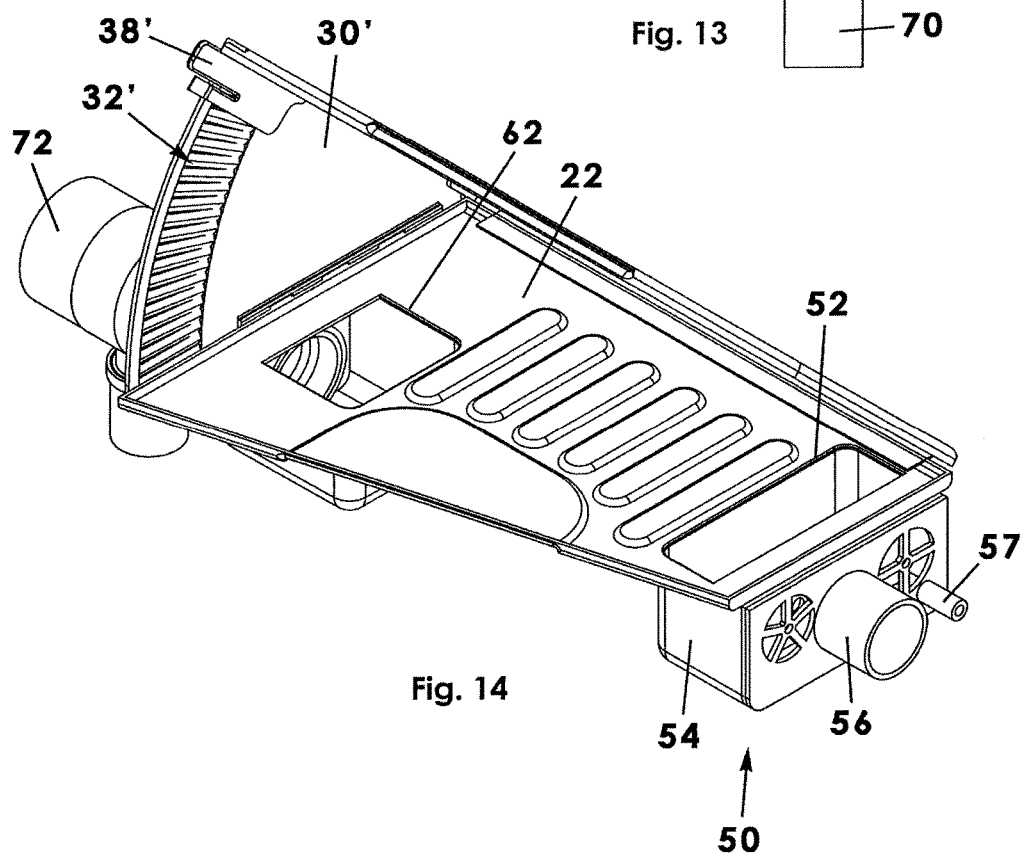
FIG. 14 is a perspective view of the resuscitation apparatus as in FIG. 13 illustrating the volume control plate and volume limit arm and with the top plate in a fully open configuration and the bellows wall removed for clarity.

As the top plate 24 is pivotally moved toward the bottom plate 22, the flexible bellows wall 27 and respective first and second end walls 28, 29 may be collapsed or folded in an accordion, folded, or collapsible manner. The inflow port 50 is operatively coupled to the housing 20 proximate the first end wall 28 so as to be in fluid communication with ambient air outside the housing 20 and with the interior area of the housing 20. In an embodiment, the bottom plate 22 may define an inflow opening 52 adjacent the first end wall 28 in communication with an inflow chamber 54 (FIG. 14). The inflow port 50 may include an inflow conduit 56 having an inlet exterior of the housing 20 and an outlet in communication with the inflow chamber 54. When the top plate 24 is moved upwardly or away from the bottom plate 22, ambient air is sucked into the inflow chamber 54 and into the interior area via the inflow opening 52. In addition, a supplemental oxygen port 57 may be included adjacent the inflow conduit 56 and is configured to allow enriched oxygen to be delivered into the interior area of the housing 20 and, ultimately, delivered to the patient.

Similarly, the bottom plate 22 may define an outflow opening 62 adjacent the second end wall 29 in communication with an outflow chamber 64 (FIG. 14). The outflow port 60 may include a outflow conduit 66 in communication with the outflow chamber 64. When the top plate 24 is moved downwardly toward the bottom plate 22, ambient air inside the interior area of the housing 20 is forced through the outflow chamber 64 and into the outflow conduit 66. It is understood that the outflow conduit 66 may be connected to a patient port 70 configured to be inserted onto a device such as a mask or tube in order to provide air or oxygen to a patient in need of emergency breathing assistance, the structure and configuration of which will be described later in further detail.

A volume control plate 30 is coupled to the housing 20, preferably to the bottom plate 22, and extends in an upright configuration adjacent the second side wall 29. The volume control plate 30 is situated outside the housing 20 so as to be easily accessible for a user to select a desired volume of air to be expelled via the outflow port 60 each time the top plate 24 is compressed against the bottom plate 22. The volume control plate 30 includes a plurality of volume selectors 32 spaced apart, each volume selector 32 having a structure for being selected and, as a result, for limiting a volume of air to be expelled. The volume control plate 30 may have an outwardly extending convex configuration.

In an embodiment, the volume control plate 30 may define a plurality of apertures 36 spaced apart along a peripheral edge of the volume control plate 30. Indicia 34 indicative of specific volumes of air may be imprinted on a surface of the volume control plate 30. A volume limit arm 38 may be pivotally coupled to the bottom plate 22 of the housing 20 at pivot point 21 and operatively coupled to the volume control plate 30 and is movable between the plurality of volume selectors 32 and configured to be coupled to a selected volume selector 32. The volume limit arm 38 may have a planar configuration in the form of a tab or handle (middle portion 38a). The volume limit arm 38 may include an attachment member which will be referred to as a nub 39 having a configuration capable of being selectively received in a selected aperture 36 of the volume control plate 30. When the nub 39 is engaged in a selected aperture 36, the volume limit arm 38 is held stationary. The volume limit arm 38 may be constructed of a semi-flexible material such that it may be bent or flexed to an extent so that the nub 39 is disengaged from an aperture 36 and the volume limit arm 38 is free to be moved along the volume control plate 30 to another selected position. Preferably, the volume limit arm 38 is constructed of a semi-rigid material such as polypropylene plastic although metal materials such as aluminum or spring steel may also work.

A volume limiting flange 40 is coupled to the upper portion of the volume limit arm 38. The volume limiting flange 40 is positioned, at least at one point, in a common vertical plane with the front edge of the top plate 24 so as to prevent upward movement of top plate 24. In other words, the volume limiting flange 40 is a "stop" to upward movement of the top plate 24 of the housing 20. For instance, when the volume limit arm 38 is set at 500 mL (FIG. 5a) as described above and the top plate 24 is moving upwardly toward a fully open configuration, the volume limiting flange 40 is contacted by the front edge 25 of the top plate 24 where the two components share a common vertical plane—thus, preventing further upward movement of top plate 24. The volume limiting flange 40, by contrast, does not prevent said top plate 24 from moving downwardly to the fully closed configuration bearing against the bottom plate 22 (FIG. 6a).

Figure 2C:
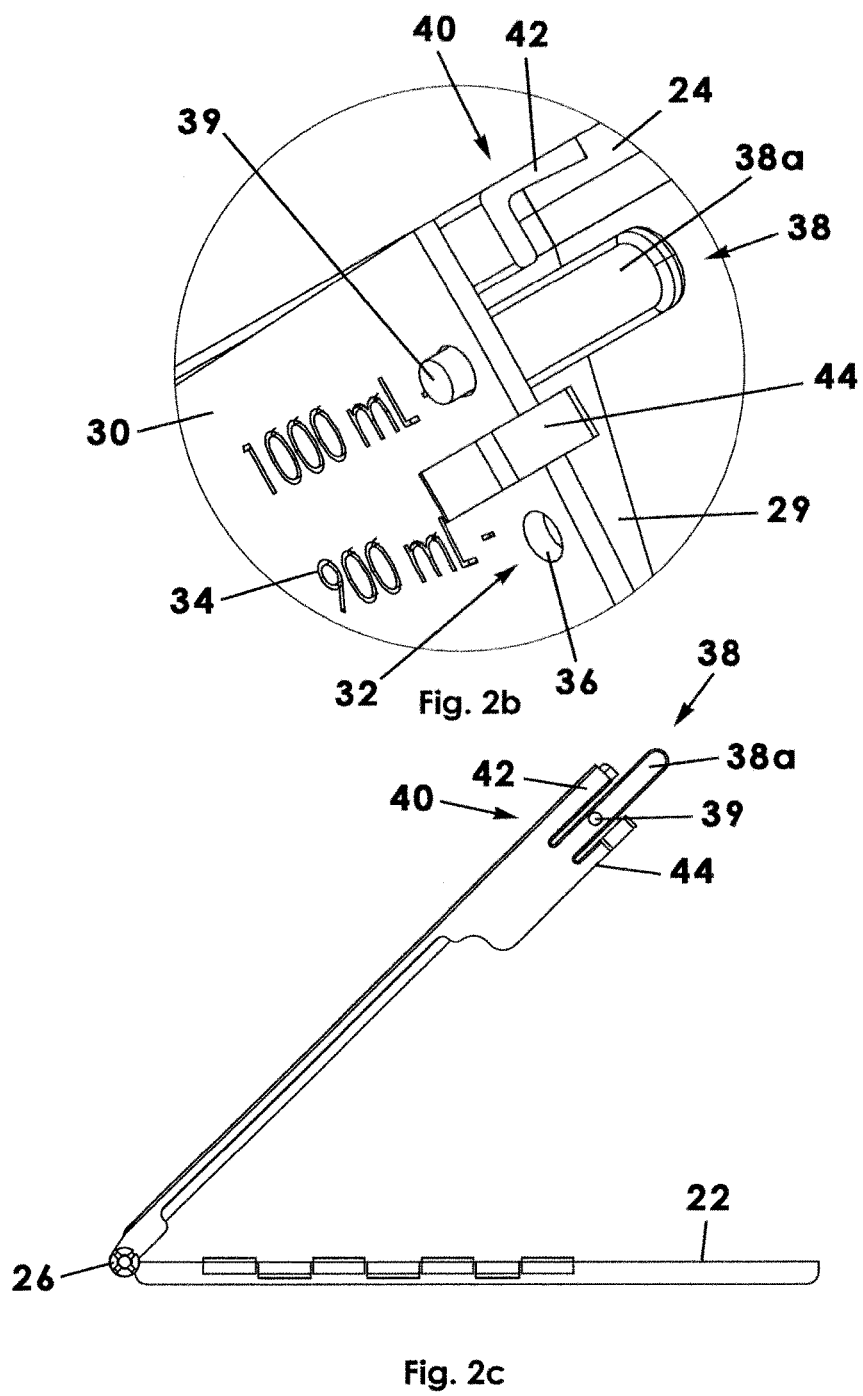
FIG. 2c is a front end view with the control plate removed for clarity, illustrating the configuration of the volume control arm.
Figure 3A:
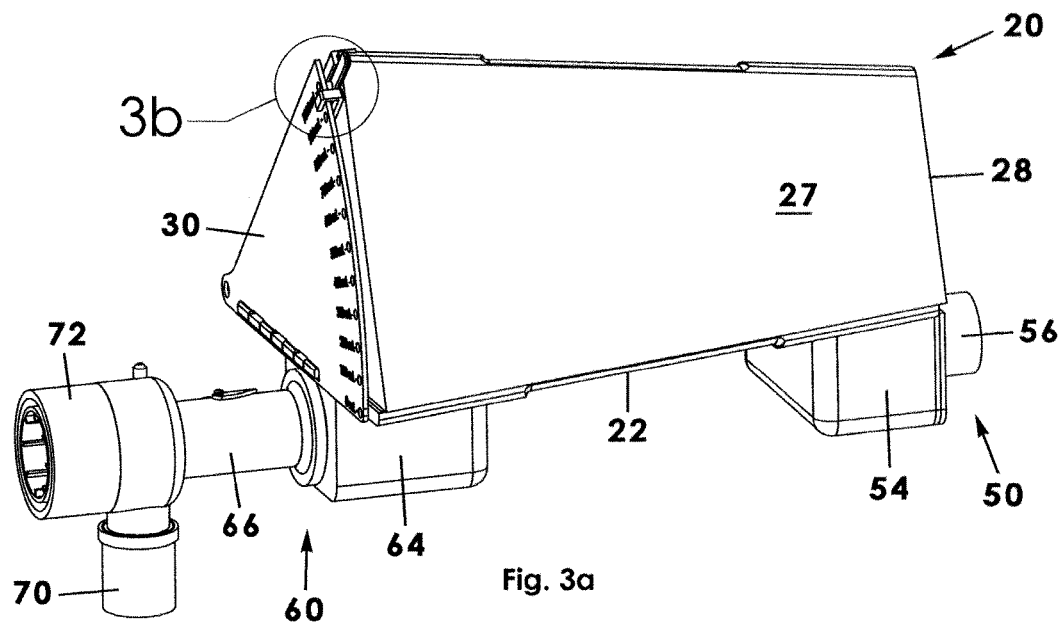
FIG. 3a is a perspective view of the resuscitation apparatus as in FIG. 2a, illustrated with a volume limit arm in a disengaged configuration relative to a volume control plate.
Figure 3B:
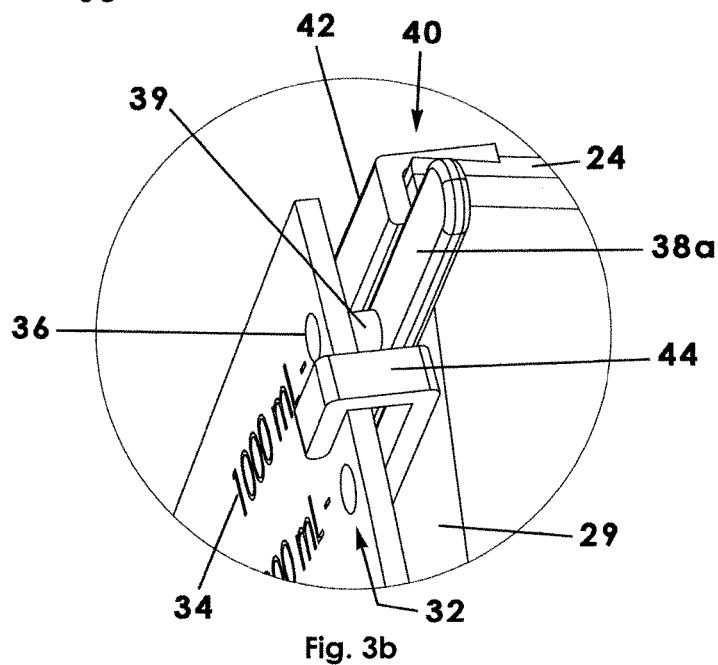

It will be understood that the upper portion of the volume limit arm 38 and volume limiting flange 40 may have a unitary or integrated construction (FIG. 2c). Further, the volume limiting flange 40 is connected to the upper portion 42 of the volume limiting arm 38 having an elongate linear configuration positioned between an inner surface of the volume control plate 30 and the second end wall 29 of the housing 20. The volume limiting flange 40 may have an inverted L-shaped configuration adapted to receive a front edge 25 of the top plate 24 and prevent the top plate 24 from upward movement beyond where the volume limit arm 38 has been set—so that over-inflation of a patient's lungs is avoided. The volume limit arm 38 may also include a lower portion 44 having a proximal end coupled to a middle portion 38a. In other words, the lower portion 44 includes an extension having a bended configuration enveloping or bending around the peripheral edge of the volume control plate 30. The extension of the lower portion 44 of the volume limit arm 38 is adjacent to a front surface of the volume control plate 30, the distal end configured to guide the volume limit arm 38 along the peripheral edge of the volume control plate 30 when the volume limit arm 38 is operated. Together, the volume control plate 30, volume limit arm 38, and volume limiting flange 40 may be referred to together as a volume control assembly.

Figure 7A:
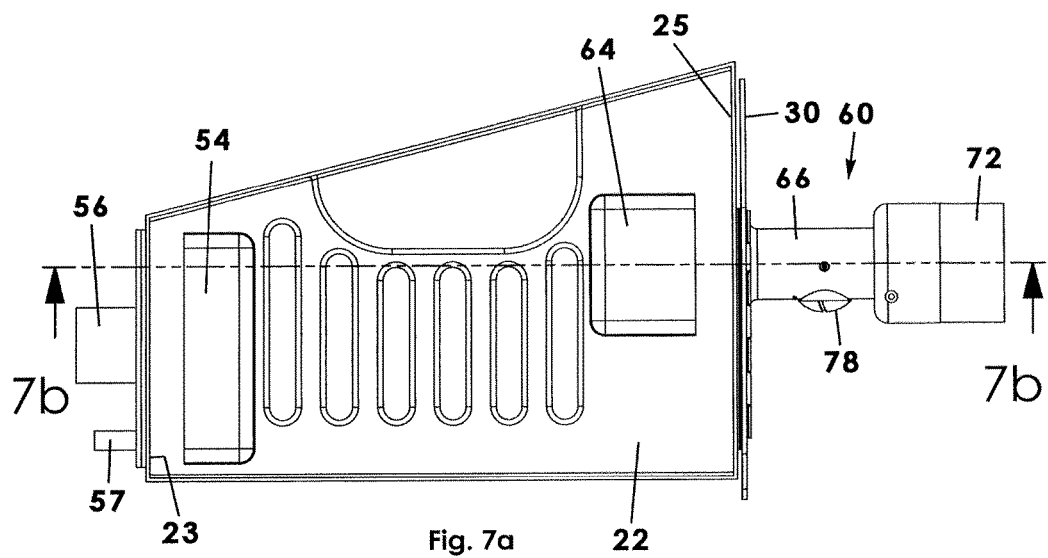
FIG. 7a is a top view of the resuscitation apparatus as in FIG. 1 with the top plate removed.
Figure 7B:
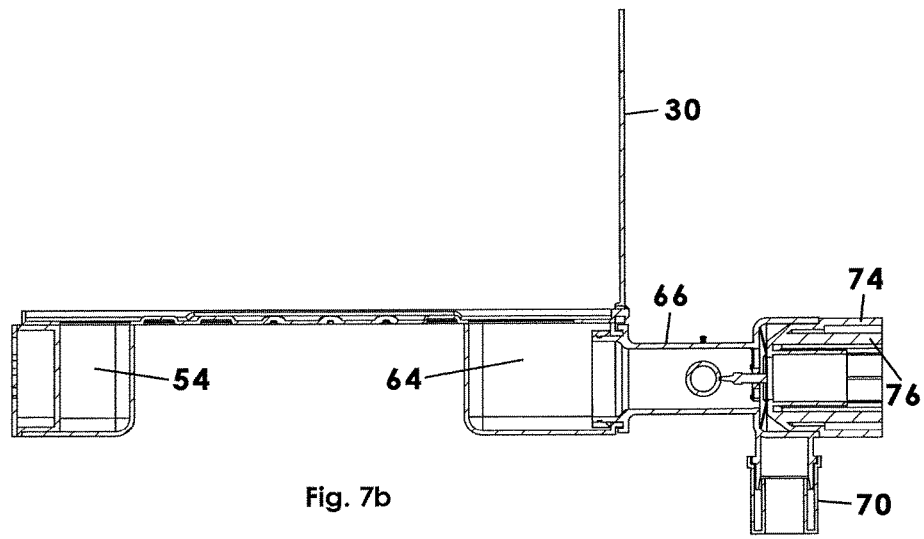
Figure 8A:
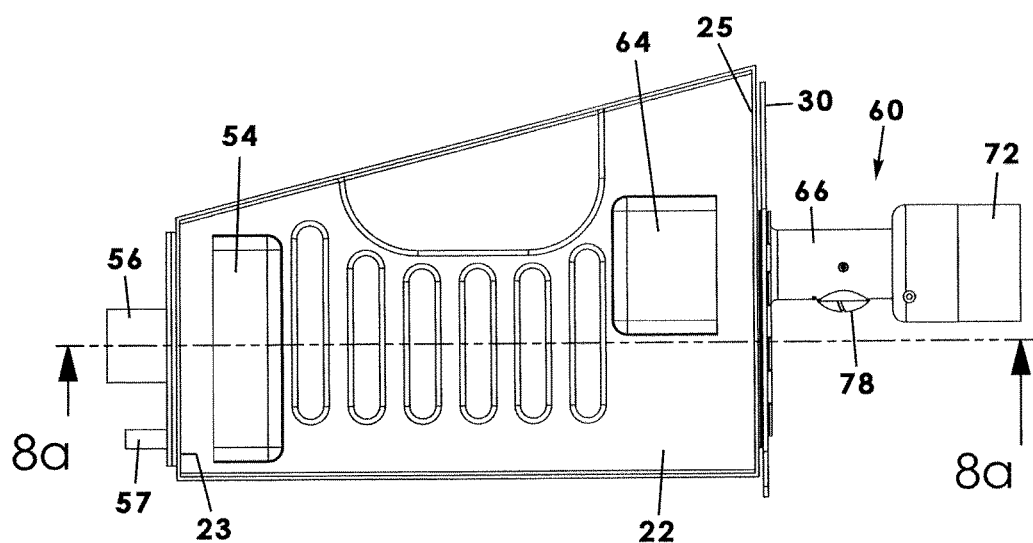
FIG. 8a is a top view of the resuscitation apparatus as in FIG. 1 with the top plate removed.
Figure 8B:
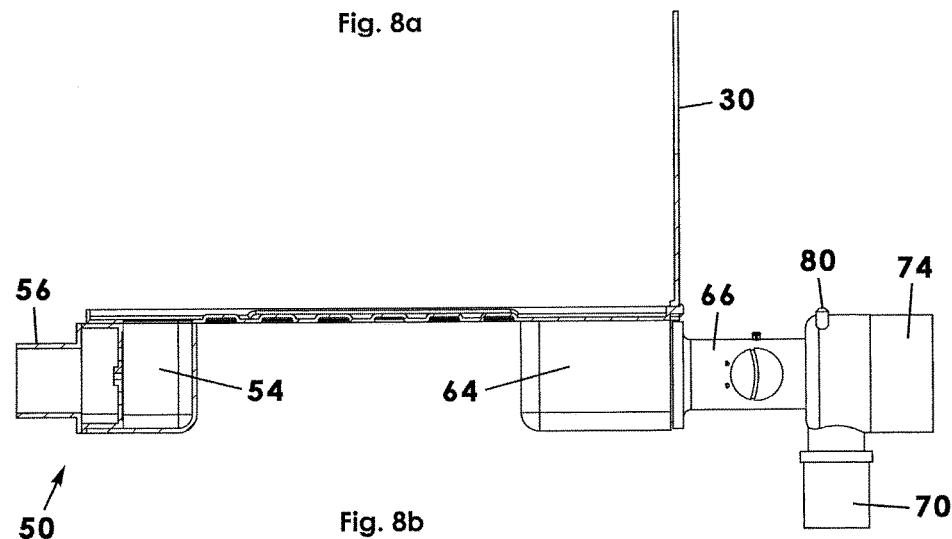
Figure 9:
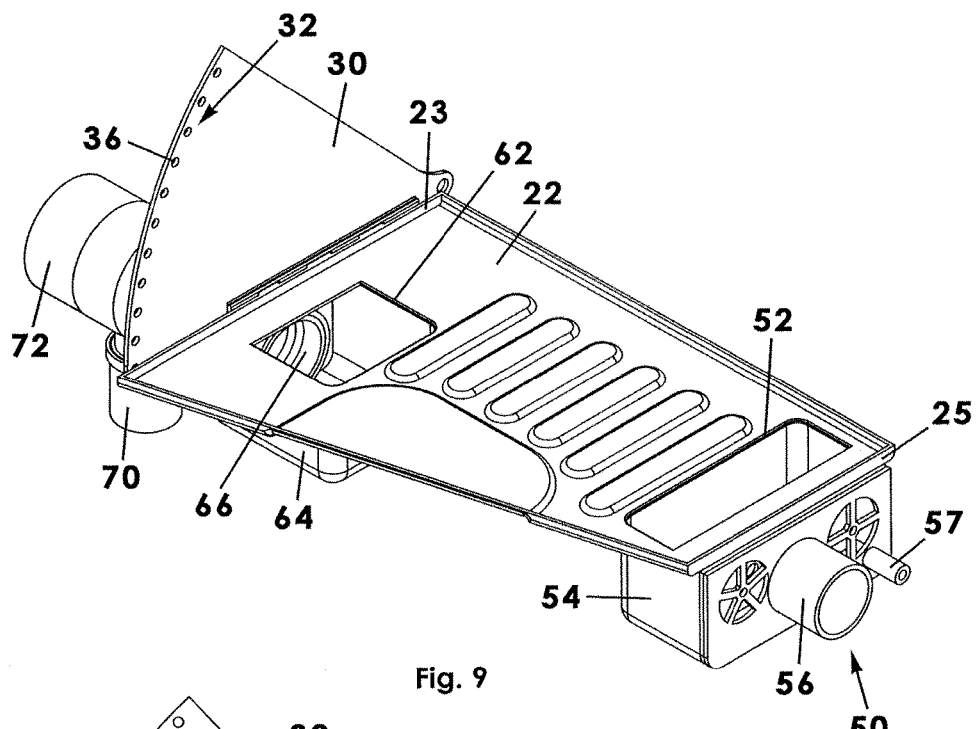
FIG. 9 is a perspective view of the resuscitation apparatus as in FIG. 1 from a reverse angle and illustrated with the top plate of the housing removed for clarity.
Figure 10:
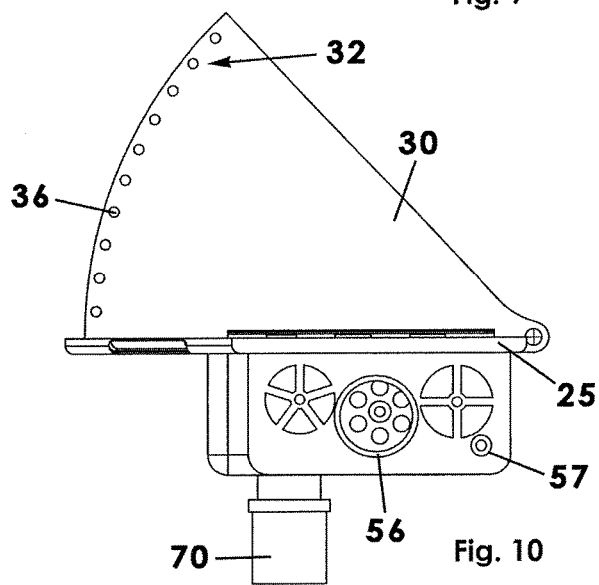
FIG. 10 is an inflow-end view of the resuscitation apparatus as in FIG. 9.
Figures 11, 12:
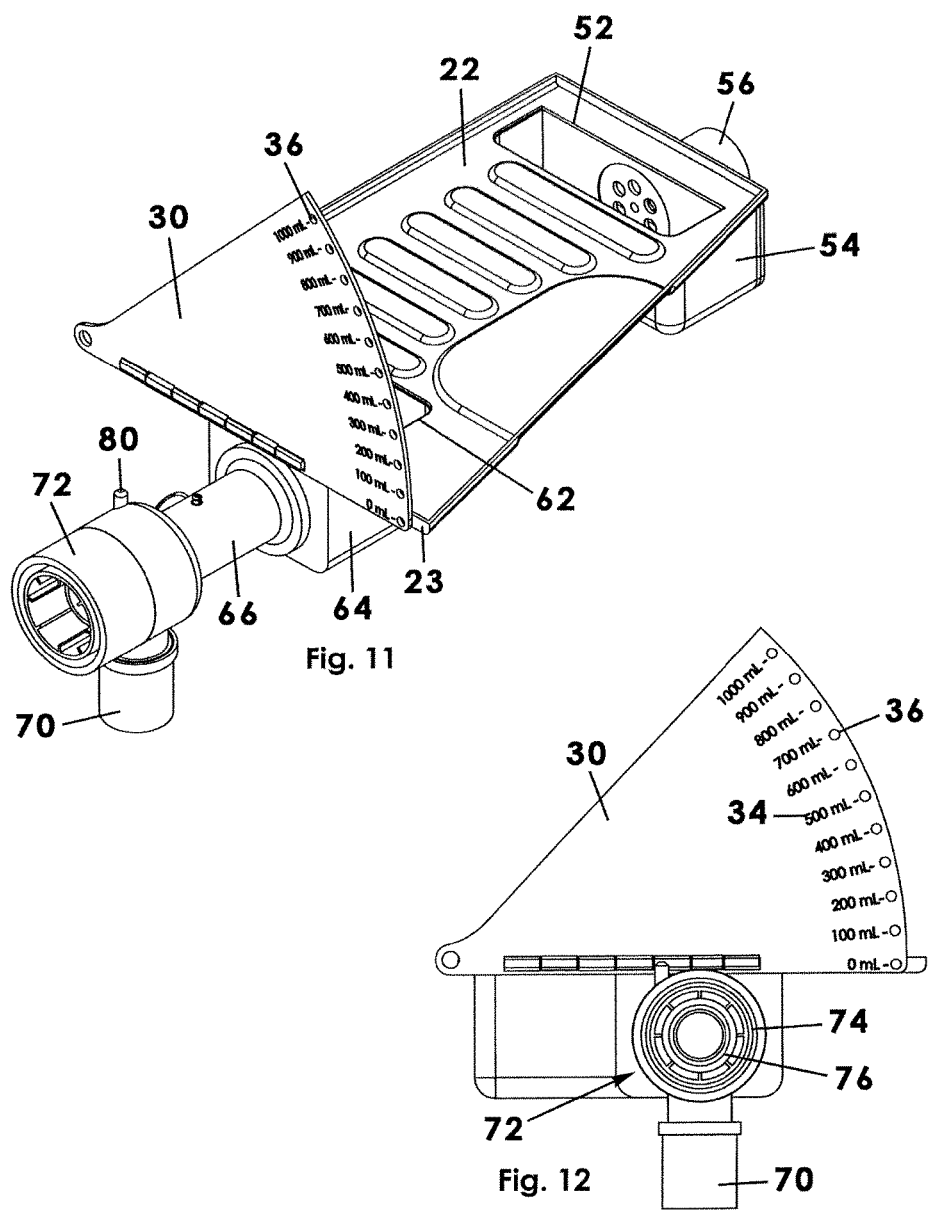
FIG. 11 is a perspective view of the resuscitation apparatus as in FIG. 1, illustrated with the top plate of the housing removed for clarity.
FIG. 12 is an outflow-end view of the resuscitation apparatus as in FIG. 11.
Figure 13:
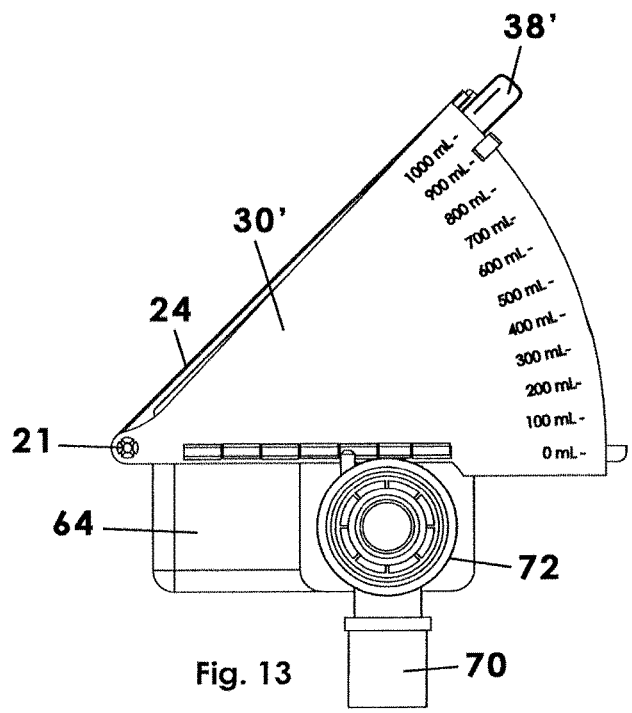
FIG. 13 is an outflow-end view of a resuscitation apparatus according to an alternative embodiment of the volume control plate and volume limit arm.

Now, with emphasis on the geometry and position of various components, respective conduits of the inflow port 50 and outflow port 60 each define an imaginary longitudinal axis, each axis being parallel to the other (FIG. 7a). The proximal side edges of the top plate 24 are also parallel with the longitudinal axis of respective inflow and outflow conduits. By contrast, the first and second end walls 28, 29 and volume control plate 30 are perpendicular to the longitudinal axis of respective inflow and outflow conduits. Accordingly, the bellows (housing) may be operated from a side angle when considered relative to the inflow port 50 and outflow port 60. Preferably, an operator of the resuscitation apparatus 10 will stand proximate the bellows wall 27 while repeatedly pressing down on the top plate 24. An exterior surface of both the top plate 24 and bottom plate 22 may have a plurality of recesses or texture so as to enhance a user's grip during use or to be ergonomic.

In another aspect, a patient port 70 extends downwardly from the outflow conduit 66 of the outflow port 60 and is perpendicular to the longitudinal axis. The patient port 70 has a configuration suitable for insertion onto a device such as a mask or tube in order to provide air or oxygen to a medical patient. In other words, air forced outwardly from the interior area is communicated through the patient port 70 and ultimately directed into the airway of the patient.

In addition, the outflow port 60 includes an accessory port 72. Preferably, the accessory port 72 is positioned inline with the outflow conduit 66 and longitudinal axis defined by the outflow port 60. The accessory port 72 may include a first adapter ring 74 having a first diameter for receiving one accessory and a second adapter ring 76 having a second diameter different from the first diameter for receiving a second accessory. Preferably, the first and second adapter rings are arranged concentrically (FIG. 1). For instance, an accessory may include a device to measure carbon dioxide or to provide positive end expiatory pressure.

Still further, a pressure relief valve 78 and a pressure disabling arm 79 operatively coupled to the pressure relief valve 78 may be situated on the outflow conduit 66 of the outflow port 60. In addition, a manometer port 80 may extend from the outflow conduit 66 and is configured to allow a manometer (not shown) to be coupled to the outflow port 60 for monitoring the pressure of air being delivered through the outflow conduit 66 to a patient.

Figure 15C:
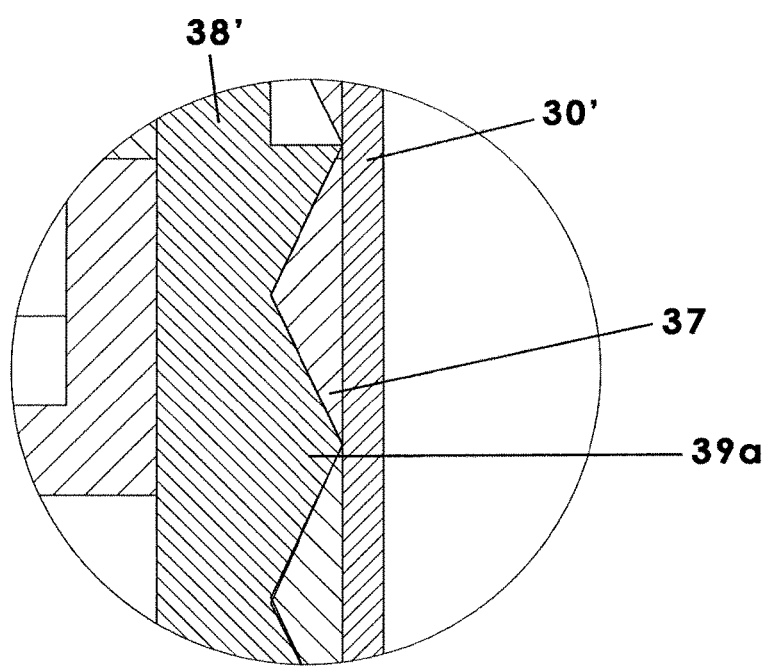
FIG. 15c is an isolated view on an enlarged scale taken from FIG. 15b.

A variation of design of the volume control plate 30' and volume limiting arm 38' is shown in FIGS. 14 to 15c. Primed numerals are used to designate the structures that are different than as described above. In this embodiment, an interior surface of the volume control plate 30' includes the plurality of volume selectors 32', the volume selectors 32' being defined by the control plate 30' as a plurality of grooves 37, teeth, notches, or recessed areas. Correspondingly, the volume limiting arm 38' may include a plurality of teeth 39a having a configuration that is complementary to a configuration of the grooves 37. It is understood that the functional operation of positioning the volume limiting arm 38' at a desired volume selector 32' is substantially the same as described above with regard to the plurality of apertures 36. Depending on the distance between adjacent groove 37, almost an infinite or analog selection and control over a selected volume is possible with this embodiment.

In use, the emergency resuscitation apparatus 10 may be used by medical professionals when there is a need to essentially breath for a patient, for instance in an emergency room or at the scene of an accident. Rather than having to choose between a plurality of resuscitators to find one that most closely offers a volume of air appropriate for the size of the patient, the present resuscitation apparatus 10 may be conveniently and quickly adjusted and set so that preselected and accurate volume of air is expelled through the outflow port 60 every time the top plate 24 is thrust downward against the bottom plate 22. Then, the selected amount of ambient air is drawn back into the interior area when the top plate 24 resets itself. As described above, the desired volume of air is selected and locked in by engaging the nub 39 of the volume limit arm 38 in a corresponding aperture 36. Then, the upper portion 42 of the volume limiting flange 40 stops upward movement of the top plate 24 when the interior area of the housing 20 is refilling with air.

It is understood that while certain forms of this invention have been illustrated and described, it is not limited thereto except insofar as such limitations are included in the following claims and allowable functional equivalents thereof.

The invention claimed is:

1. An emergency resuscitation apparatus with external air volume control, comprising:
   a housing that includes a bottom plate having opposed proximal and distal side edges and includes a top plate having opposed proximal and distal side edges, wherein respective proximal side edges of said bottom plate and said top plate are pivotally coupled together and selectively movable in an accordion manner between open and closed configurations;
   wherein said housing includes a bellows wall coupled to said distal edges of said bottom plate and said top plate, respectively, and includes opposed first and second end walls coupled to rear and front edges of said bottom and top plates, respectively, said bellows wall and respective first and second end walls having a flexible construction;
   wherein said housing defines an interior area;
   an inflow port operatively coupled to said housing and configured so that ambient air from outside said housing is siphoned into said interior area upon movement of said top plate away from said bottom plate;

an outflow port operatively coupled to said housing and configured so that air in said interior area is expelled therefrom upon movement of said top plate toward said bottom plate;

a volume control plate coupled to said housing externally adjacent to said second end wall and extending upwardly, said volume control plate having a plurality of volume selectors;

a volume limit arm that includes a middle portion operatively coupled to said volume control plate and selectively movable between and selectively coupled to a selected volume selector;

wherein said volume limit arm includes an upper portion having a volume limiting flange situated in a common vertical plane with said front edge of said top plate and having a configuration such that said volume limiting flange prevents movement of said top plate upwardly beyond said volume limiting flange.

2. The emergency resuscitation apparatus as in claim 1, wherein:

said volume control plate defines an outer peripheral edge;

said plurality of volume selectors are a plurality of apertures defined by said volume control plate adjacent to and spaced apart along said outer peripheral edge;

said middle portion of said volume limit arm includes a nub having a configuration selectively received in a respective aperture for releasably holding said volume limit arm at a selected position relative to said volume control plate.

3. The emergency resuscitation apparatus as in claim 2, wherein:

said volume limiting flange of said upper portion of said volume limit arm has an elongate linear configuration configured to selectively receive said front edge of said top plate and prevent upward movement of said top plate beyond a setting of said volume limit arm;

a lower portion of said volume limit arm includes a proximal end having an extension coupled to and extending outwardly from said middle portion and a distal end having a bended configuration adjacent a front surface of said volume control plate adjacent said outer peripheral edge thereof.

4. The emergency resuscitation apparatus as in claim 3, wherein said lower portion of said volume limit arm captures said peripheral edge of said volume control plate and guides said volume limit arm along said peripheral edge.

5. The emergency resuscitation apparatus as in claim 2, wherein said outer peripheral edge has a convex configuration.

6. The emergency resuscitation apparatus as in claim 2, wherein said volume limit arm is constructed of a semi-rigid material that is resilient to selectively release said nub from engagement in a respective aperture.

7. The emergency resuscitation apparatus as in claim 1, wherein said volume limiting flange is a stop to upward movement of said top plate so as to limit a volume of air expelled from said interior area via said outflow port.

8. The emergency resuscitation apparatus as in claim 1, further comprising indicia on said volume control plate adjacent respective selectors, said indicia being indicative of a volume of air to be expelled from said interior area upon a movement of the housing to a closed configuration.

9. The emergency resuscitation apparatus as in claim 1, wherein said top plate is pivotally coupled to said bottom plate with one of a living hinge or a bonded spine.

10. The emergency resuscitation apparatus as in claim 1, wherein:

said inflow port and said outflow port each define an imaginary longitudinal axis, each longitudinal axis being parallel to the other;

wherein said opposed side edges of said top plate are parallel to each longitudinal axis and said volume control plate is perpendicular to each longitudinal axis such that said top plate is operated downwardly from a side angle in use.

11. The emergency resuscitation apparatus as in claim 1, further comprising a patient port having a configuration suitable for use with a mask or tube to provide air or oxygen to a patient.

12. The emergency resuscitation apparatus as in claim 11, further comprising an accessory port in fluid communication with said outflow port and inline therewith;

wherein said accessory port includes a first adapter ring having a first diameter and a second adapter ring having a second diameter different than the diameter of said first adapter ring, said first and second adapter rings situated concentrically.

13. The emergency resuscitation apparatus as in claim 1, wherein said top plate includes an outer surface having a no-slip ergonomic surface.

14. The emergency resuscitation apparatus as in claim 1, wherein:

said inflow port is operatively coupled to said housing proximate said first end wall and in fluid communication with said interior area and with air outside said interior area and configured so that ambient air is siphoned into said interior area upon movement of said top plate away from said bottom plate;

said outflow port is operatively coupled to said housing proximate said second end wall and in fluid communication with said interior area and configured so that air in said interior area is expelled from said interior area upon movement of said top plate toward said bottom plate.

15. The emergency resuscitation apparatus as in claim 1, wherein said respective proximal side edges of said bottom plate and said top plate are coupled together with one of a living hinge or bonded spine that defines an imaginary horizontal axis, said top plate being selectively movable about said imaginary horizontal axis between fully closed and fully open configurations.

16. The emergency resuscitation apparatus as in claim 1, wherein:

said volume control plate defines an outer peripheral edge;

said plurality of volume selectors are a plurality of grooves defined by an interior surface of said volume control plate adjacent to and spaced apart along said outer peripheral edge;

said volume limit arm includes a plurality of teeth having a configuration complementary to and selectively received in a respective groove for releasably holding said volume limit arm at a selected position.

17. The emergency resuscitation apparatus as in claim 16, wherein:

said volume limiting flange of said upper portion of said volume limit arm has an elongate linear configuration configured to selectively receive said front edge of said top plate and prevent upward movement of said top plate beyond set position of said volume limit arm;

said volume limit arm includes a lower portion having a proximal end coupled to and extending outwardly from said middle portion and a distal end having a bended configuration adjacent a front surface of said volume control plate adjacent said outer peripheral edge thereof.

18. An emergency resuscitation apparatus with external air volume control, comprising
   a housing that includes a bottom plate having opposed proximal and distal side edges and includes a top plate having opposed proximal and distal side edges, wherein respective proximal side edges of said bottom plate and said top plate are pivotally coupled together and selectively movable in an accordion manner between open and closed configurations;
   wherein said housing includes a bellows wall coupled to said distal edges of said bottom plate and said top plate, respectively, and includes opposed first and second end walls coupled to front and rear edges of said bottom and top plates, respectively, said bellows wall and respective first and second end walls having a flexible construction;
   wherein said housing defines an interior area capable of receiving ambient air;
   an inflow port operatively coupled to said housing and configured so that ambient air from outside said housing is siphoned into said interior area upon movement of said top plate away from said bottom plate;
   an outflow port operatively coupled to said housing and configured so that air in said interior area is expelled therefrom upon movement of said top plate toward said bottom plate; and
   a volume control assembly operatively coupled to an exterior surface of said housing adjacent said second end wall, said volume control assembly including a volume control plate having a plurality of volume selectors and a volume limit arm selectively coupled to a respective volume selector for selecting a maximum volume of air expelled from said interior area;
   wherein said volume control assembly includes a volume limiting flange coupled to said volume limit arm, said volume limiting flange being situated in a common vertical plane with said front edge of said top plate so that said volume limiting flange prevents movement of said top plate upwardly beyond said volume limiting flange;
   wherein:
      said volume control plate includes a peripheral edge and said plurality of volume selectors are a plurality of apertures spaced apart along said peripheral edge;
      said volume limit arm includes a nub having a configuration selectively received in a respective aperture configured to releasably hold said volume limit arm at a selected position.

19. An emergency resuscitation apparatus with external air volume control, comprising:
   a housing that includes a bottom plate having opposed proximal and distal side edges and includes a top plate having opposed proximal and distal side edges, wherein respective proximal side edges of said bottom plate and said top plate are pivotally coupled together and selectively movable in an accordion manner between open and closed configurations;
   wherein said housing includes a bellows wall coupled to said distal edges of said bottom plate and said top plate, respectively, and includes opposed first and second end walls coupled to front and rear edges of said bottom and top plates, respectively, said bellows wall and respective first and second end walls having a flexible construction;
   wherein said housing defines an interior area capable of receiving ambient air;
   an inflow port operatively coupled to said housing and configured so that ambient air from outside said housing is siphoned into said interior area upon movement of said top plate away from said bottom plate;
   an outflow port operatively coupled to said housing and configured so that air in said interior area is expelled therefrom upon movement of said top plate toward said bottom plate; and
   a volume control assembly operatively coupled to an exterior surface of said housing adjacent said second end wall, said volume control assembly including a volume control plate having a plurality of volume selectors and a volume limit arm selectively coupled to a respective volume selector for selecting a maximum volume of air expelled from said interior area;
   wherein said volume control assembly includes a volume limiting flange coupled to said volume limit arm, said volume limiting flange being situated in a common vertical plane with said front edge of said top plate so that said volume limiting flange prevents movement of said top plate upwardly beyond said volume limiting flange.

20. The emergency resuscitation apparatus as in claim 19, wherein said volume limit arm includes:
   an upper portion including said volume limiting flange having an elongate linear configuration configured to selectively receive said front edge of said top plate and prevent upward movement of said top plate beyond a respective selected position of said volume limit arm; and
   a lower portion having an extension extending outwardly and having a bended configuration that surrounds a peripheral edge of said volume control plate and guides said volume limit arm along said peripheral edge when said volume limiting arm is moved.

* * * * *